(12) United States Patent
Leung et al.

(10) Patent No.: US 9,931,493 B2
(45) Date of Patent: *Apr. 3, 2018

(54) CORROSION-RESISTANT MAGNETIC ARTICLE

(71) Applicant: Medtronic Xomed, Inc., Jacksonville, FL (US)

(72) Inventors: Chun Man Alan Leung, Jacksonville, FL (US); William Jeffrey Bertrand, Goleta, CA (US); Drew Powell Amery, Jacksonville, FL (US); Lori C. Speckman, Goleta, CA (US); Thomas J. Sierocuk, Jacksonville, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/119,937

(22) PCT Filed: Jan. 21, 2016

(86) PCT No.: PCT/US2016/014303
§ 371 (c)(1),
(2) Date: Aug. 18, 2016

(87) PCT Pub. No.: WO2016/118735
PCT Pub. Date: Jul. 28, 2016

(65) Prior Publication Data
US 2017/0056631 A1 Mar. 2, 2017

Related U.S. Application Data

(63) Continuation-in-part of application No. 14/603,027, filed on Jan. 22, 2015.

(51) Int. Cl.
*A61M 27/00* (2006.01)
*A61L 31/10* (2006.01)
(Continued)

(52) U.S. Cl.
CPC ........ *A61M 27/006* (2013.01); *A61L 31/022* (2013.01); *A61L 31/028* (2013.01);
(Continued)

(58) Field of Classification Search
None
See application file for complete search history.

(56) References Cited

U.S. PATENT DOCUMENTS

| 4,508,760 A | 4/1985 | Olson et al. |
| 4,758,288 A | 7/1988 | Versic |

(Continued)

FOREIGN PATENT DOCUMENTS

| CN | 102140666 A | 8/2011 |
| CN | 202463036 U | 10/2012 |

(Continued)

OTHER PUBLICATIONS

Derwent Abstract of DE 10-2004-058451-A1 (Year: 2004).*
(Continued)

*Primary Examiner* — Kevin M Bernatz
(74) *Attorney, Agent, or Firm* — Patterson Thuente Pedersen, P.A.

(57) ABSTRACT

A magnetic article with a corrosion resistant barrier formed from a poly (tetrafluoro-p-xylene) conformal coating or from a parylene conformal coating having a melting point of at least about 430° C. and a moisture vapor transmission less than about 0.5 g-mm/m²/day at 90% RH and 37° C., the conformal coating being covered with a polysulfone thermoplastic overlayer.

27 Claims, 4 Drawing Sheets (51) Int. Cl.
   *A61L 31/02* (2006.01)
   *C09D 5/08* (2006.01)
   *C09D 165/04* (2006.01)
   *A61L 31/14* (2006.01)
   *H01F 1/057* (2006.01)
   *H01F 7/02* (2006.01)
   *H01F 41/02* (2006.01)
   *H01F 1/055* (2006.01)

(52) U.S. Cl.
   CPC ............... *A61L 31/10* (2013.01); *A61L 31/14* (2013.01); *C09D 5/08* (2013.01); *C09D 165/04* (2013.01); *H01F 1/055* (2013.01); *H01F 1/057* (2013.01); *H01F 7/02* (2013.01); *H01F 41/026* (2013.01); *A61L 2420/00* (2013.01); *A61L 2420/02* (2013.01); *A61L 2420/08* (2013.01); *A61M 2207/00* (2013.01)

(56) References Cited

U.S. PATENT DOCUMENTS

| | | | |
|---|---|---|---|
| 5,069,972 A | 12/1991 | Versic | |
| 5,154,978 A * | 10/1992 | Nakayama | B05D 1/60 427/129 |
| 5,879,808 A * | 3/1999 | Wary | B05D 1/60 257/E23.144 |
| 6,106,894 A | 8/2000 | Zapf | |
| 6,703,462 B2 * | 3/2004 | Lee | C08G 61/025 526/242 |
| 7,223,228 B2 | 5/2007 | Timm et al. | |
| 7,976,271 B2 | 7/2011 | LaRose et al. | |
| 7,997,854 B2 | 8/2011 | LaRose et al. | |
| 8,152,493 B2 | 4/2012 | LaRose et al. | |
| 8,512,013 B2 | 8/2013 | LaRose et al. | |
| 9,775,974 B2 * | 10/2017 | Leung | A61L 31/10 |
| 2005/0267324 A1 | 12/2005 | Timm et al. | |
| 2008/0050581 A1 * | 2/2008 | Miwa | C09D 5/08 428/332 |
| 2008/0200750 A1 * | 8/2008 | James | A61M 1/101 600/16 |
| 2008/0200811 A1 * | 8/2008 | Wakabayashi | A61B 8/12 600/459 |
| 2011/0224805 A1 | 9/2011 | Schulman et al. | |
| 2013/0045146 A1 * | 2/2013 | Peters | B01L 3/5635 422/527 |
| 2013/0345646 A1 | 12/2013 | Bertrand et al. | |
| 2014/0377939 A1 * | 12/2014 | Khachatryan | G02F 1/133305 438/479 |
| 2015/0348685 A1 * | 12/2015 | Hu | C22C 33/02 75/246 |
| 2016/0213898 A1 * | 7/2016 | Leung | A61L 31/022 |
| 2016/0308405 A1 * | 10/2016 | Thompson | H01F 1/00 |

FOREIGN PATENT DOCUMENTS

| | | | | |
|---|---|---|---|---|
| CN | 202771884 U | 3/2013 | | |
| CN | 202816528 U | 3/2013 | | |
| CN | 203014504 U | 6/2013 | | |
| CN | 203415343 U | 1/2014 | | |
| CN | 103805993 A | 5/2014 | | |
| DE | 102004058451 A1 * | 6/2006 | ........... | H01F 41/026 |
| EP | 1 743 602 A1 | 1/2007 | | |
| WO | WO 90/02604 | 3/1990 | | |
| WO | WO 02/20293 A2 | 3/2002 | | |
| WO | WO 2005/110281 A2 | 11/2005 | | |

OTHER PUBLICATIONS

International Search Report for PCT/US2016/014303 dated May 12, 2016.
Dexter Magnetics Neodymium Iron Boron Rare Earth Magnets and Material Grades (2014) web page downloaded from: http://www.dextermag.com/material-grades/neodymium-iron-boron-magnets.
Drak et al., Corrosion of Nd—Fe—B permanent magnets, Jamme, 20, issues 1-2 (Jan.-Feb. 2007).
K&J Magnetics—Specifications undated web page downloaded from: https://www.kjmagnetics.com/specs.asp on May 6, 2014.
Kisco Conformal Coating, LLC Parylene Properties (2011) web page downloaded from: http://www.kiscoparylene.com/parylenes/parylene-properties.
Kisco diX Parylenes Oxygen permeability, Vapor transmission & Water absorption (2009) web page downloaded from: http://www.kiscoparylene.com/sites/www.kiscoparylene.com/files/uploads/Permeability_Absorption_Percentage.pdf.
Kisco Parylenes Thermal Properties (2009) web page downloaded from: http://www.kiscoparylene.com/sites/www.kiscoparylene.com/files/uploads/Thermal_Properties.pdf.
SCS Parylene Coatings (2014) web page downloaded from: http://scscoatings.com/what_is_parylene/parylene_properties.aspx.
SCS Medical Coatings (2011).
SCS Parylene Properties (2007).
Solvay Technical Bulletin Quick Guide to Injection Molding Udel® PSU, Radel® PPSU, Veradel® PESU, Acudel® modified PPSU (2013) downloaded from: http://www.solvayplastics.com/sites/solvayplastics/EN/Solvay%20Plastics%20Literature/DPG_Sulfones_Quick_Molding_Guide_EN.pdf.
Derwent Abstract of WO2014/101747 A1 (pub. 2014).
PCT/US2016/049030 International Search Report and Written Opinion.
O'Grady, *Sulfonated Polyethersulfone as a New Platform for Thin Film Components* (2013), available at digitalcommons.uconn.edu/cgi/viewcontent.cgi?article=1466&context=gs_theses.
Radel-PPSU-Veradel-PESU-Acudel-PPSU-Design-Guide (2014), available at solvay.com/en/binaries/Radel-PPSU-Veradel-PESU-Acudel-PPSU-Design-Guide_EN-227541.pdf.
PCT/US2016/014303 International Search Report and Written Opinion.
Related case U.S. Appl. No. 14/603,027 Office Action dated Jan. 9, 2017.

* cited by examiner

CORROSION-RESISTANT MAGNETIC ARTICLE

CROSS-REFERENCE TO RELATED APPLICATION

This application is a national stage filing under 35 U.S.C. § 371 of International Application No. PCT/US2016/014303 filed Jan. 21, 2016, which claims priority under 35U.S.C. § 119 to U.S. patent application Ser. No. 14/603,027 filed Jan. 22, 2015, the disclosures of both of which are incorporated herein by reference.

FIELD OF THE INVENTION

This invention relates to coated, magnetic articles.

BACKGROUND

U.S. Patent Application Publication No. U.S. 2013/0345646 A1 (Bertrand et al.) describes an implantable physiological shunt system which utilizes a magnetic coupling between an external adjustment tool and an internal magnetic rotor assembly in order to control the flow of fluids. The shunt system can include a locking feature to prevent unintended setting changes when the shunt is exposed to strong external magnetic fields.

This feature can be particularly important when shunts used to control the flow of cerebrospinal fluid (CSF) from the brain ventricles of hydrocephalus patients are exposed to external magnetic fields during magnetic resonance imaging (MRI). However, if the shunt lock is set, the internal magnet may also be prevented from aligning with the external magnetic field, and in a sufficiently strong external magnetic field may become demagnetized or reverse magnetized. If this occurs, surgical replacement of the shunt may be required.

External magnetic fields of for example as high as 3 Tesla are generated in some MRI scanners. Fields of that strength can demagnetize or reverse magnetize samarium cobalt (SmCo) magnetic materials. NdFeB (Neodymium) rare earth permanent magnets have sufficiently high coercivity ($H_{ci}$) to resist demagnetization or reverse magnetization in such fields, but also have very poor corrosion resistance. Magnetic strength generally is lost in direct proportion to the mass loss caused by corrosion. NdFeB magnets typically are made more resistant to corrosion by applying protective coatings such as plating (e.g., nickel plating or layers of copper and nickel plating), powder coatings or paints. However, when such protectively coated NdFeB magnets are submersed in aqueous saline solution, the protective coating may in some cases be breached within 24 hours after the start of exposure.

SUMMARY

The disclosed invention provides, in one aspect, a magnetic article comprising an NdFeB magnet having thereon a substantially continuous corrosion resistant barrier comprising a fluorinated parylene conformal coating covered with a polysulfone thermoplastic overlayer.

The disclosed invention provides, in another aspect, a magnetic article comprising an NdFeB magnet having thereon a substantially continuous corrosion resistant barrier comprising a parylene conformal coating having a melting point of at least about 430° C. and a moisture vapor transmission less than about 0.5 g-mm/m²/day at 90% RH and 37° C., the parylene conformal coating being covered with a polysulfone thermoplastic overlayer.

The disclosed invention provides, in yet another aspect, a method for making a coated magnetic article, which method comprises vapor depositing upon an NdFeB magnet a layer or layers of a fluorinated parylene conformal coating, and applying molten polysulfone over the conformal coating, to provide a substantially continuous corrosion resistant barrier over the magnet.

The disclosed invention provides, in a further aspect, a method for making a coated magnetic article, which method comprises vapor depositing upon an NdFeB magnet a layer or layers of a parylene conformal coating having a melting point of at least about 430° C. and a moisture vapor transmission less than about 0.5 g-mm/m²/day at 90% RH and 37° C., and applying molten polysulfone over the parylene conformal coating, to provide a substantially continuous corrosion resistant barrier over the magnet.

The disclosed invention provides, in another aspect, an implantable medical device containing a coated magnetic article comprising an NdFeB magnet having thereon a substantially continuous corrosion resistant barrier comprising a fluorinated parylene conformal coating covered with a polysulfone thermoplastic overlayer.

The disclosed invention provides, in yet another aspect, an implantable medical device containing a coated magnetic article comprising an NdFeB magnet having thereon a substantially continuous corrosion resistant barrier comprising a parylene conformal coating having a melting point of at least about 430° C. and a moisture vapor transmission less than about 0.5 g-mm/m²/day at 90% RH and 37° C., covered with a polysulfone thermoplastic overlayer.

BRIEF DESCRIPTION OF THE DRAWING

Like reference symbols in the various figures of the drawing indicate like elements. The elements in the drawing are not drawn to scale.

DETAILED DESCRIPTION

The following detailed description describes certain embodiments and is not to be taken in a limiting sense. The terms shown below have the following meanings:

The recitation of a numerical range using endpoints includes all numbers subsumed within that range (e.g., 1 to 5 includes 1, 1.5, 2, 2.75, 3, 3.80, 4, 5, etc.).

The terms "a," "an," "the," "at least one," and "one or more" are used interchangeably. Thus, for example, an article coated with "a" layer means that the article may be coated with "one or more" layers.

When words of orientation such as "atop", "on", "uppermost", "underlying" and the like are used herein to refer to various elements in the disclosed coated articles, they identify the relative position of an element with respect to a horizontally-disposed, upwardly-facing substrate or support for such element. It is not intended that the disclosed coated articles should have any particular orientation in space during or after their manufacture.

The term "barrier" refers to a layer or layers of material that impede the transmission of gases (e.g., oxygen, air or water vapor), liquids (e.g., water) or ions (e.g., sodium or chlorine ions) into or out of a substrate or support.

The term "coating" means a thin (e.g., less than 0.5 mm average thickness) layer covering at least a portion of a support or substrate.

The term "condensing" means collecting vapor-phase material in a liquid or solid state on a support or substrate.

The term "corrosion resistant" when used with respect to a barrier on an NdFeB magnet means that the magnet does not exhibit visible corrosion after 2 days immersion in 37° C. normal saline solution.

The term "conformal" when used with respect to a coating on a substrate or support means that the coating has the same shape as the underlying substrate or support topography including features such as crevices, points and edges.

The term "continuous" when used with respect to a barrier, coating, overlayer or overmolding on a substrate or support means that the barrier, coating, overlayer or overmolding covers the underlying substrate or support without measurable gaps, fissures, pin-holes or other discontinuities in coverage that would directly expose the substrate or support to external gases (e.g., ambient air) or external fluids (e.g. in the case of an implantable medical device, bodily fluids). The term "substantially continuous" means that the barrier, coating, overlayer or overmolding covers the underlying substrate or support without gaps, fissures or other discontinuities in coverage that are visible to the naked eye.

The term "dimer" refers to an oligomer that is a combination of two monomers.

The term "hermetic" refers to a material that is substantially impermeable, for the typical projected working life of the disclosed magnetic articles, to the transmission of corrosion-inducing quantities of gases (e.g., oxygen, air or water vapor) and fluids (e.g., water).

The term "magnet" refers to an article having a volume of at least 1 mm³ and magnetic or magnetizable properties.

The term "monomer" refers to a single unit molecule that is capable of combining with itself or with other monomers or oligomers to form other oligomers or polymers.

The term "oligomer" refers to a compound that is a combination of 2 or more (and typically 2, 3 or 4 up to about 6) monomers, but that might not yet be large enough to qualify as a polymer.

The term "overlayer" refers to a thin (e.g., less than 0.5 mm average thickness) or thick (e.g., more than 0.5 mm average thickness) layer of a material atop a substrate or support. Such a layer may be formed using a thermoplastic material by for example melting and dip-coating, melting and spray-applying, or melting and injection molding the thermoplastic material over the support or substrate. The overlayer may be separated from the substrate or support by a conformal coating such as the poly(tetrafluoro-p-xylene) conformal coating discussed above, and by one or more optional additional layers atop or underlying the conformal coating. The overlayer may have a constant or variable thickness. If present, a variable thickness may arise from one or more features in the support or substrate that penetrate below or project beyond the support or substrate average thickness, or from one or more features in the overlayer that penetrate below or project beyond the covering average thickness. Exemplary such features may include grooves, notches, detents, apertures, splines, tabs, stops, steps, sealing surfaces, pivot points, axles, bearing surfaces, indicators to depict direction (e.g., of fluid flow or magnetization), spring retaining collars, valves, valve actuators and other recesses or protrusions.

The term "overmolding" refers to an overlayer made by injection molding.

The term "polymer" refers to an organic molecule that has multiple regularly or irregularly arranged carbon-containing monomer or oligomer repeating units.

The terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

Figure 1:
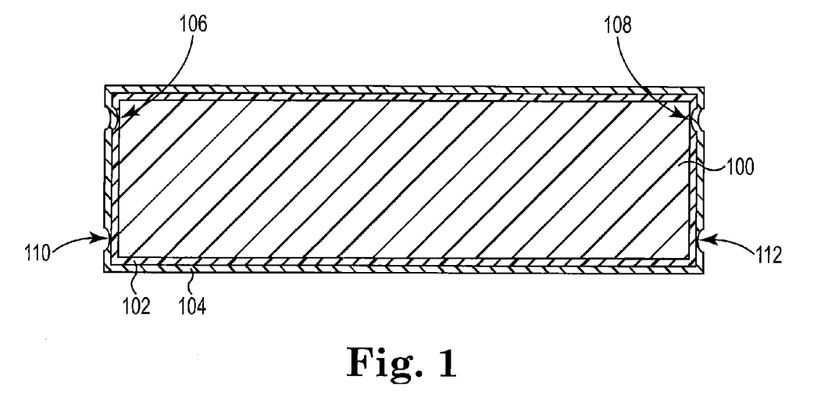
FIG. 1 is a side cross-sectional view of an NdFeB magnet coated with a poly(tetrafluoro-p-xylene) conformal coating.

FIG. 1 is a side cross-sectional view of a free-standing NdFeB magnet 100. Magnet 100 serves as a substrate or support upon which may be formed the above-mentioned conformal coating, shown in FIG. 1 as poly(tetrafluoro-p-xylene) layers 102 and 104. For illustrative purposes, layers 102 and 104 have been depicted with exaggerated thickness. Layers 102 and 104 may have the same or different average thicknesses, and may for example each be at least about 1, at least about 2, at least about 5, at least about 10 or at least about 20 micrometers thick, and may for example each be less than about 100, less than about 80, less than about 60, less than about 50 or less than about 40 micrometers thick. Small discontinuities 106, 108 in portions of layer 102 and small discontinuities 110, 112 in portions of layer 104 are artifacts arising from contact with a gripping fixture (not shown in FIG. 1) that supported magnet 100 during the formation of layers 102 and 104. Different fixtures, different grip positions or both desirably are employed prior to the formation of each such layer to ensure that discontinuities 106, 108, 110 and 112 are each confined to only small portions of layers 102 or 104 without overlap, so as to enable the overall formation of a continuous conformal coating.

Figure 2:
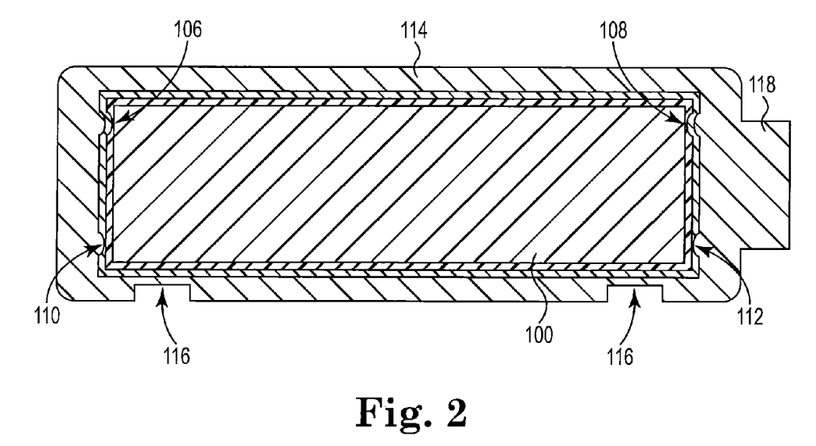
FIG. 2 is a side cross-sectional view of the FIG. 1 magnet covered with a polysulfone thermoplastic overlayer.

FIG. 2 is a side cross-sectional view of magnet 100 from FIG. 1 in which layer 104 has been covered with polysulfone thermoplastic overlayer 114. Overlayer 114 desirably has an average thickness at least several times greater (e.g., at least 2×, at least 3×, at least 5× or at least 10× greater) than the combined thickness of the layers 102 and 104. As depicted in FIG. 2, overlayer 114 includes features 116 and 118 respectively representing recesses below and protrusions beyond the average thickness of overlayer 110.

Figure 3A:
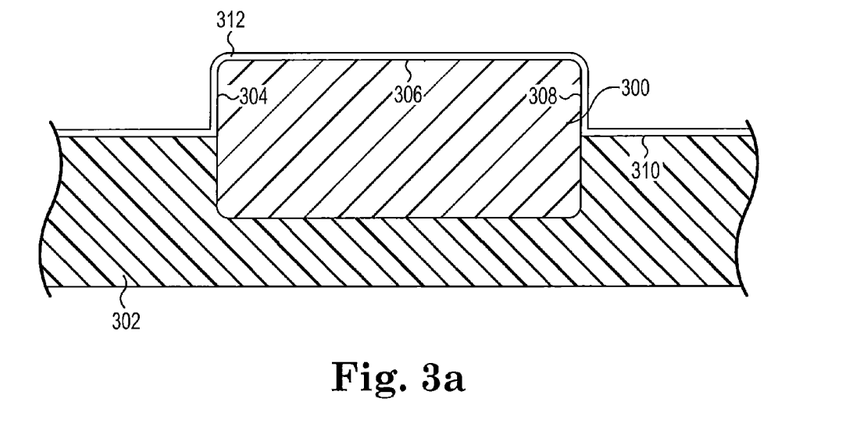
FIG. 3a is a side cross-sectional view of a partially potted NdFeB magnet whose unpotted surfaces are coated with a poly(tetrafluoro-p-xylene) conformal coating.
Figure 3B:
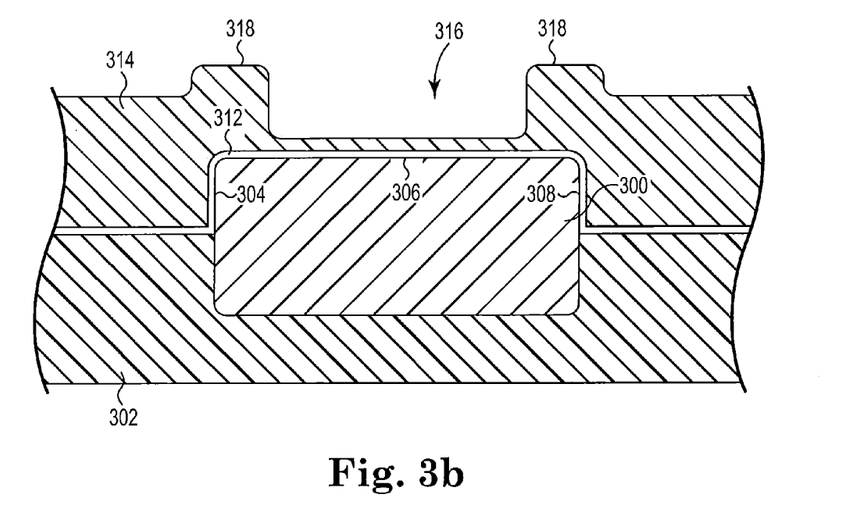
FIG. 3b is a side cross-sectional view of the FIG. 3a magnet with a polysulfone thermoplastic overlayer.

FIG. 3a and FIG. 3b are side cross-sectional views of another embodiment of the disclosed magnetic article. As shown in FIG. 3a, NdFeB magnet 300 has been partially potted in potting material 302. Potting material 302 may be formed from a variety of non-magnetic materials, e.g. zinc, aluminum or various hardenable organic potting compounds. Potting material 302 desirably is sufficiently thick and made from a material suitable to provide a hermetic structure with respect to the portions of magnet 300 contacted by potting material 302. In addition, potting of magnet 300 in potting material 302 desirably does not unduly detract from the magnetic or magnetizable properties of magnet 300. Unpotted magnet surfaces 304, 306 and 308 and the upper face 310 of potting material 302 have been coated with a layer 312 of a poly(tetrafluoro-p-xylene) conformal coating. During the application of conformal coating 312, magnet 300 may be fixtured by for example gripping potting material 302 and accordingly the application of a single layer of coating 312 can provide a continuous coating over the exposed portions of magnet 300. If desired, some or the entire exposed upper surface of potting compound 302 may be masked prior to application of coating material 312, with the mask being removed prior to subsequent processing. In another embodiment, excess coating material 312 may be removed from some or the entire exposed upper surface of potting compound 302 after application of coating material 312 (e.g., using solvents, abrasives or other techniques that will be familiar to persons having ordinary skill in the art). As depicted in FIG. 3a, no mask has been applied and no coating material 312 has been removed, and consequently portions of layer 312 extend away from magnet 300 and lie atop potting compound 302.

As shown in FIG. 3b, layer 312 has been covered with polysulfone thermoplastic overlayer 314. As depicted in FIG. 3b, overlayer 314 includes features 316 and 318 respectively representing a recess below and protrusions beyond the average thickness of overlayer 314.

Figure 4A:
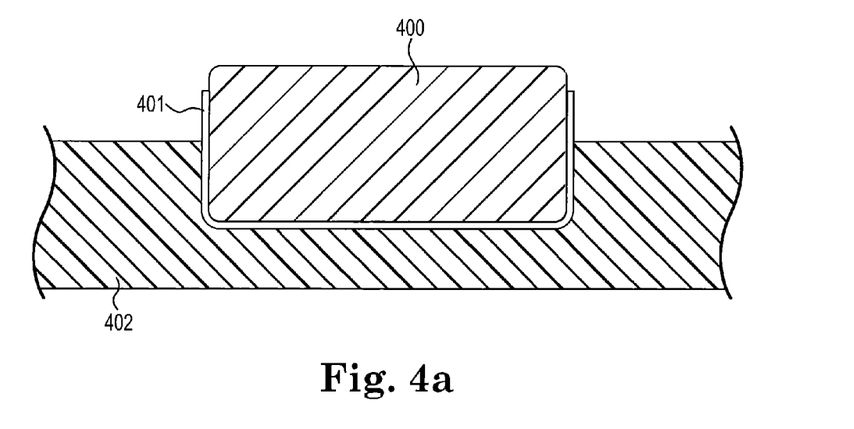
FIG. 4a is a side cross-sectional view of a partially potted NdFeB magnet that has been partially coated with a poly(tetrafluoro-p-xylene) conformal coating.
Figure 4B:
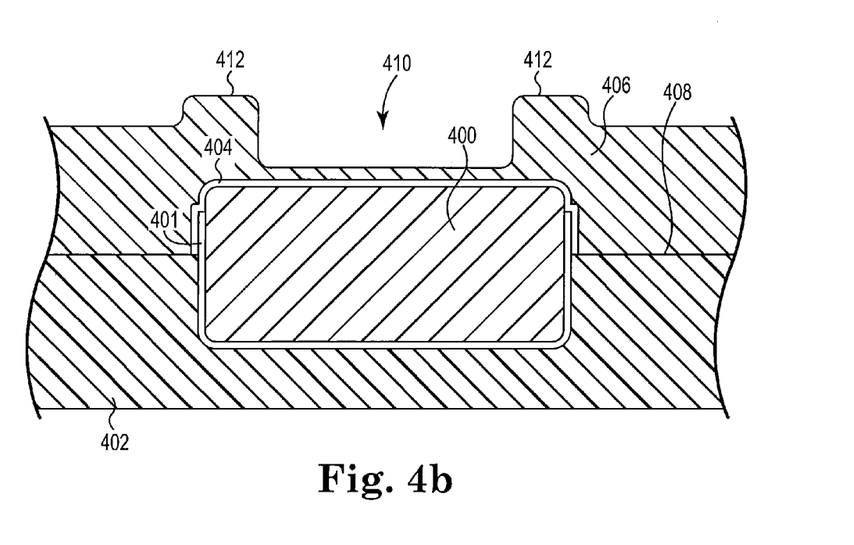
FIG. 4b is a side cross-sectional view of the FIG. 4a magnet with a further poly(tetrafluoro-p-xylene) conformal coating and a polysulfone thermoplastic overlayer.

FIG. 4a and FIG. 4b are side cross-sectional views of another embodiment of the disclosed magnetic article. As shown in FIG. 4a, NdFeB magnet 400 has been partially coated with a layer 401 of a poly(tetrafluoro-p-xylene) conformal coating. The uncoated portion of magnet 400 is an artifact arising from contact with a gripping fixture (not shown in FIG. 4a) that supported magnet 400 during the formation of layer 401. Potting material 402 contacts the submerged portion of layer 401. Potting material 402 may be formed from a variety of non-magnetic materials, e.g. zinc, aluminum or various hardenable organic potting compounds, and desirably is formed (e.g., molded) from polysulfone.

As shown in FIG. 4b, the portions of magnet 400 and layer 401 that were exposed in FIG. 4a have been covered with a layer 404 of an additional poly(tetrafluoro-p-xylene) conformal coating. As also shown in FIG. 4b, potting material 402 and layer 404 have been covered with a polysulfone thermoplastic overlayer 406. A mask (not depicted in FIG. 4b) has been used to limit the extent of layer 404 and prevent layer 404 from covering portions of potting material 402 that were exposed in FIG. 4a. A variety of masking techniques may be employed, and with care can provide embodiments in which layers 401 and 404 merge to provide a single layer of apparently uniform thickness. Boundary 408 represents the contact area between potting material 402 and overlayer 406.

When potting material 402 and overlayer 406 are both made from polysulfone, boundary 408 desirably is not discernible due to melting of a portion of potting material 402 and merger with overlayer 406 when overlayer 406 is formed. As depicted in FIG. 4b, overlayer 406 includes features 410 and 412 respectively representing a recess below and protrusions beyond the average thickness of overlayer 406.

Figure 5:
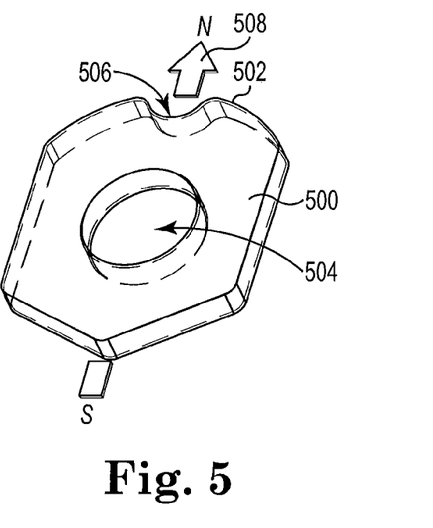
FIG. 5 is a perspective view, partially in phantom, of an NdFeB ring magnet coated with a poly(tetrafluoro-p-xylene) conformal coating.
Figure 6:
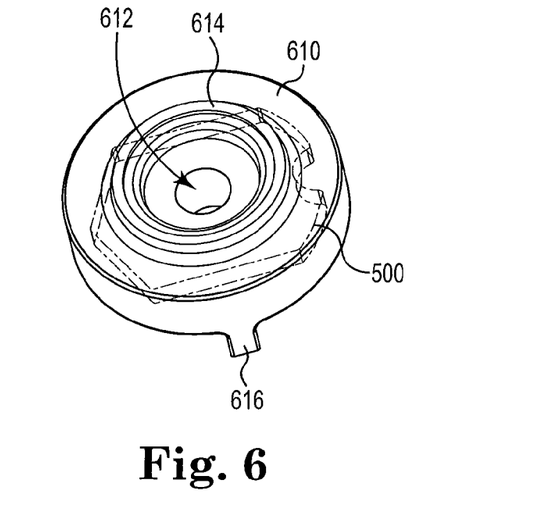
FIG. 6 is a perspective view, partially in phantom, of the FIG. 5 magnet covered with a polysulfone thermoplastic overlayer.

FIG. 5 and FIG. 6 are perspective views, partially in phantom, of another embodiment of the disclosed magnetic article. As shown in FIG. 5, NdFeB ring magnet 500 has been coated with a poly(tetrafluoro-p-xylene) conformal coating 502. Magnet 500 includes central aperture 504 and notch 506. Arrow 508 depicts the direction of magnetization for magnet 500.

As shown in FIG. 6, magnet 500 from FIG. 5 has been covered with a polysulfone thermoplastic overlayer 610. As depicted in FIG. 6, overlayer 610 includes aperture 612 through the center of magnet 500, spring retaining collar 614 which protrudes above the remainder of magnet 500, and valve actuation tab 616 which protrudes below the remainder of magnet 500.

A variety of NdFeB magnets may be used to make the disclosed magnetic articles and implantable medical devices. The magnet may be a monolithic, homogenous solid article made for example by molding or machining the chosen NdFeB alloy. The magnet may instead be a non-homogenous article made for example by sintering together particles of the chosen NdFeB alloy or by molding such particles in a suitable binder. In some embodiments solid magnets may be preferred so as to maximize their magnetic strength. The magnet may have a variety of sizes, and may for example have a volume of at least 2, at least 5, at least 10 or at least 25 mm$^3$.

The magnet may have a variety of magnetic properties, and may for example have a magnetic strength (Maximum Energy Product or BH$_{max}$) of at least 28, at least 30, at least 32 or at least 35 Mega Gauss Oersteds (MGOe), The magnet may also or instead have an Intrinsic Coercive Force (H$_{ci}$) of at least 10, at least 14, at least 20, at least 25, at least 30 or at least 35kiloOersteads (kOe). The magnet may also or instead have a Curie Temperature (T$_c$) of at least 300, at least 310, at least 320 or at least 330° C. In some embodiments, H$_{ci}$ values of at least 25, at least 30 or at least 35 may be preferred so as to reduce the likelihood of demagnetization due to externally-applied magnetic fields such as MRI fields. In some embodiments including smaller volume magnets covered with a thick injection-molded polysulfone overlayer, T$_c$ values at least 310, at least 320 or at least 330° C. may be preferred so as to reduce the likelihood of demagnetization during the overlayer formation step. The magnet may if desired be demagnetized during processing (e.g., for ease in machining, or as a consequence of heat applied during magnet processing), and remagnetized at a later time (e.g., before, between or after the conformal coating or overlayer formation steps).

The magnet may have a variety of shapes including balls, bars, rods (e.g., cylinders), rings, partial rings (e.g., horseshoes) and plates (e.g., rectangles). The magnet may have a major planar surface or major axis with a polarity of magnetization parallel to or at an angle with respect to such major planar surface or major axis.

Exemplary magnetic material suppliers include Alliance, LLC, Dexter Magnetics, Magstar Technologies, Inc., Inc., Hitachi Corporation, Dailymag Motor (Ningbo) Limited, Ningbo Xinfeng Magnet Industry Co., Ltd., Shenzhen Feiya Magnet Co., Ltd. and Yuyao Keyli Magnetics Co., Ltd.

The disclosed magnetic devices may employ a variety of conformal coatings. In some embodiments the parylene is fluorinated, e.g., with fluorine atoms on the aromatic rings (viz., fluoroaromatic groups), fluoroaliphatic groups between the aromatic rings, or both. In some such embodiments the aromatic rings, the fluoroaliphatic groups, or both are perfluorinated, and thus have no hydrogen atoms. Suitable fluorinated parylene conformal coating materials include poly(tetrafluoro-p-xylene) which may be obtained under the generic name parylene AF-4, with Formula I shown below:

—[CF$_2$C$_6$H$_4$CF$_2$]$_n$—     I.

Exemplary commercially available parylene AF-4 materials include Parylene HTTM, from Specialty Coating Systems, Inc., which is said by its manufacturer to have an MP greater than 500° C., and an MVT of 0.22 at 100% relative humidity (RI-I) and 38° C.

Another suitable parylene AF-4 material is diX SFTM parylene from Kisco Conformal Coating, LLC, which is said by its manufacturer to have an MP of 450° C. and an MVT of 0.21 at 37° C. Other suitable fluorinated parylenes may be obtained under the generic names parylene VT-4, with Formula II shown below:

—[CH$_2$C$_6$F$_4$CH$_2$]$_n$—     II.

In some embodiments the parylene has a melting point (MP) of at least about 430° C., and a moisture vapor transmission (MVT) less than about 0.5 g-mm/m$^2$/day at 90% RH and 37° C. Some of the fluorinated parylenes described above also satisfy these conditions. In some embodiments the parylene has an MP of at least about 450° C., at least about 475° C. or at least about 500° C. In some embodiments the parylene may also or instead have an MVT less than about 0.4 or less than about 0.3 g-mm/m$^2$/day at 90% RH and 37° C. Suitable parylenes having a melting point of at least about 430° C. and a moisture vapor transmission less than about 0.5 g-mm/m$^2$/day at 90% RH and 37° C. include diX CFTM parylene from Kisco Conformal Coating, LLC, which is said by its manufacturer to have an MP of 434° C. and an MVT of 0.28 at 37° C. This parylene may also be a fluorinated parylene, but it is said by its manufacturer to have a proprietary formula and its structure does not appear to have been published.

Coatings made using the parylene preferably are rated as being thermally stable, or as being suitable for continuous service, at temperatures of at least 200° C., at least 250° C. or at least 300° C. in air, or at temperatures of least 300° C., at least 350° C. or at least 400° C. in an oxygen-free environment.

The parylene conformal coating typically is formed by converting a solid parylene dimer into vapor-phase parylene radicals using a vaporizer and pyrolizer, and depositing the radicals onto the exposed surface or surfaces of the NdFeB magnet in a suitable deposition or coating chamber. The conformal coating procedures described in U.S. Pat. Nos. 4,508,760 (Olson et al.), 4,758,288 (Versic '288) and 5,069,972 (Versic '972) may be adapted for that purpose, while bearing in mind that these patents describe parylene deposition onto microparticles or microcapsules rather than onto discrete magnets, and that the non-halogenated or chlorinated parylenes they employ have lower melting points and may have lower dimer vaporization temperatures than the parylenes described above. Additional parylene coating procedures are described in the 2007 Specialty Coating Systems, Inc. Technical Brochure entitled "SCS Parylene Properties" and in the 2011 Specialty Coating Systems, Inc. Technical Brochure entitled "SCS Medical Coatings".

The thus-formed parylene coating or coatings may range from angstroms to micrometers or mils in thickness and may for example have a thickness of about 2 to 100 pin per coating layer or layers. For magnets that can be supported or otherwise fixtured without covering any of the surface to be coated, the disclosed magnetic articles preferably have at least one conformal coating layer. For magnets that require a support or other fixture that covers part of the surface to be coated, the disclosed magnetic articles may have at least two conformal coating layers, with relocation or refixturing of the magnet being carried out between application of the first and subsequent layer or layers so as to ensure full coverage. Surface pretreatments or primer coatings (e.g., plasma etching pretreatments or organic silane primers applied from solution or by vapor deposition) may be used prior to deposition of the parylene conformal coating or between coating layers. The parylene conformal coating may if desired include dyes, indicators or other adjuvants, e.g. to facilitate inspection and confirm attainment of a continuous conformal coating layer. The parylene conformal coating may if desired be annealed (e.g., at about 300° C. for parylene AF-4 materials) to increase crystallinity and thereby improve physical properties such as cut-through resistance, hardness or abrasion resistance.

The disclosed magnetic devices may employ a variety of polysulfone materials. Exemplary polysulfones include crystalline or amorphous materials, such as polyethersulfone (PES, PSU or PESU), sulfonated polyethersulfone (SPES or SPSF) and polyphenylsulfone (PPSF or PPSU). Exemplary polysulfones include UDEL™ PSU, VERADEL™ PESU and RADEL™ PPSU, ACUDEL™ modified PPSU and EPISPIRE™ HTS high-temperature sulfone from Solvay Plastics. Low to medium viscosity or high to medium flow rate injection molding grades such as UDEL P-1700, UDEL P-1710, UDEL P-1750 MR, UDEL P-3700 HC PES, UDEL P-3703, VERRADEL 3250 MR, VERADEL 3300 PREM, VERADEL 3400, VERADEL A-301, RADEL R-5000, RADEL R-5100, RADEL R-5600, RADEL R-5800, RADEL R-5900, RADEL R-5900 MR, RADEL R-7159, RADEL R-7300, RADEL R-7400, RADEL R-7535, RADEL R-7558 and RADEL R-7625 (all from Solvay Plastics) are preferred for some embodiments. The disclosed implantable medical devices preferably are made using a polysulfone material approved for use in medical devices by the applicable regulatory agencies.

The polysulfone overlayer may be formed using a variety of techniques that will be familiar to persons having ordinary skill in the art, with injection molding using a one-shot or multiple-shot (e.g., two-shot) process being preferred for some embodiments, and dip coating, powder coating, spray coating or other techniques sufficient to encapsulate or otherwise cover the parylene conformal coating being preferred for other embodiments. The polysulfone overlayer may have a variety of average thicknesses, and may for example have an average thickness of at least 0.5 mm, at least 1 mm, at least 2 mm or at least 5 mm. The polysulfone overlayer may have any desired maximum average thickness coincident with attaining sufficient magnetic strength in the coated magnetic article, and may for example be less than 100 mm, less than 50 mm, less than 25 mm, less than 10 mm, less than 5 mm or less than 1 mm. The recommended melting or molding temperature typically will vary depending on factors including the chosen magnetic material, chosen parylene, chosen polysulfone, and (when used), the chosen mold. The polysulfone may be dried prior to melting or molding, for example to provide a moisture level less than about 0.1% or less than about 0.05% in the dried product. The polysulfone melting point or molding temperature preferably is less than the parylene melting point and more preferably is also less than the magnet Curie temperature T$_c$. Polysulfone melting or molding temperatures higher than T$_c$ may cause loss of magnetic strength. However, use of a quick molding cycle, low volume overlayer or high volume magnet may ameliorate loss of strength. Remagnetization may be employed after overlayer formation to restore magnetic strength. Exemplary polysulfone drying conditions and melting or molding temperatures are described for example in the 2013 Solvay Technical Bulletin entitled "Quick Guide to Injection Molding Udel® PSU, Radel® PPSU, Veradel® PESU, Acudel® modified PPSU".

The disclosed barrier helps reduce corrosion of the magnet due to exposure to gases (e.g., oxygen, air or water vapor), liquids (e.g., water, blood or other bodily fluids) or ions (e.g., sodium or chlorine ions). In some embodiments the disclosed coated magnetic articles do not exhibit visible corrosion after 5 days, 10 days or 20 days immersion in 37° C. normal saline solution. Preferred embodiments of the disclosed magnetic articles both retain their full magnetic strength and do not exhibit visible corrosion after 5 days, 10 days, 20 days or even 28 days immersion in 87° C. normal saline solution. Inductively-coupled plasma (ICP) mass spectrophotometric analysis of the saline solutions after such immersion preferably finds no detectable magnetic elements compared to saline controls prepared without the immersed magnetic article.

The disclosed magnetic articles may be part of a detector, actuator, latch, indicator or other mechanical, electrical or other system. If housed inside or on a larger device, the magnet may be stationary or movable within or on such device, and if movable may be slidable, pivotable or rotatable. The magnet may bear upon or move another part of the device. The magnet may be a single magnet or multiple magnets within or on such device. The device may be an implantable medical device, such as the implantable CSF shunt valves described in the above-mentioned Bertrand et al. application, urethral control devices such as those shown in U.S. Pat. No. 7,223,228 B2 (Timm et al.), implantable blood pumps such as those shown in U.S. Pat. No. 8,512,013 B2 (LaRose et al.), pacemakers, implantable drug pumps, and other devices that will be familiar to persons having ordinary skill in the medical arts. If part of an implantable medical device, the device may be sold in sterile packaging and designed for one-time use. Exemplary sterilization techniques will be familiar to persons having ordinary skill in the art, and include heat, steam, chemical processes (e.g., ethylene oxide, nitrogen dioxide, bleach or various aldehydes) and irradiation (e.g., UV, gamma radiation or electron beam processing). The magnet may be part of a variety of non-implantable medical devices including hearing aids, external drug pumps and dental or orthodontic appliances (e.g., bridges, plates, dentures and orthodontic correctional devices). The magnet may also be part of a variety of non-medical devices including sensors, switches, valves, indicators or signaling devices for uses including marine, automotive and defense systems.

Other embodiments of the disclosed invention include:
A magnetic article comprising an NdFeB magnet having thereon a substantially continuous corrosion resistant barrier comprising a parylene conformal coating having a melting point of at least about 430° C. and a moisture vapor transmission less than about 0.5 g-mm/m$^2$/day at 90% RH and 37° C., the parylene conformal coating being covered with a polysulfone thermoplastic overlayer, or a method for making a coated magnetic article, which method comprises vapor depositing upon an NdFeB magnet a layer or layers of a poly(tetrafluoro-p-xylene) conformal coating, and applying a molten polysulfone overlayer over the poly(tetrafluoro-p-xylene) conformal coating, to provide a substantially continuous corrosion resistant barrier over the magnet, or a method for making a coated magnetic article, which method comprises vapor depositing upon an NdFeB magnet a layer or layers of a parylene conformal coating having a melting point of at least about 430° C. and a moisture vapor transmission less than about 0.5 g-mm/m$^2$/day at 90% RH and 37° C., and applying a molten polysulfone overlayer over the parylene conformal coating, to provide a substantially continuous corrosion resistant barrier over the magnet, or an implantable medical device containing a coated magnetic article comprising an NdFeB magnet having thereon a substantially continuous corrosion resistant barrier comprising a poly(tetrafluoro-p-xylene) conformal coating covered with a polysulfone thermoplastic overlayer, or an implantable medical device containing a coated magnetic article comprising an NdFeB magnet having thereon a substantially continuous corrosion resistant barrier comprising a parylene conformal coating having a melting point of at least about 430° C. and a moisture vapor transmission less than about 0.5 g-mm/m$^2$/day at 90% RH and 37° C., covered with a polysulfone thermoplastic overlayer, and wherein either individually or in any combination:
the magnet has a Maximum Energy Product $BH_{max}$ of at least 28 Mega Gauss Oersteds, an Intrinsic Coercive Force $H_{ci}$ of at least 10 kiloOersteads and a Curie Temperature $T_c$ of at least 300° C., or the magnet has a Maximum Energy Product $BH_{max}$ of at least 32 Mega Gauss Oersteds, an Intrinsic Coercive Force $H_{ci}$ of at least 35 kiloOersteads and a Curie Temperature $T_c$ of at least 310° C., or the magnet comprises a bar, rod, ring, partial ring or plate, or the conformal coating has a thickness of 2 to 100 µm, or the overlayer comprises polyethersulfone, or the overlayer comprises sulfonated polyethersulfone or polyphenylsulfone, or the overlayer has an average, thickness of 0.5 to 10 mm, or the overlayer has a variable thickness, or the overlayer is an overmolding, or the polysulfone melting point is less than the parylene melting point, or the polysulfone melting point is also less than the magnet Curie temperature $T_c$, or the conformal coating has a thickness less than 0.5 mm and the overlayer has an average thickness greater than 0.5 mm, or the magnet or overlayer has a recess or protrusion, or the recess or protrusion comprises a groove, notch, detent, aperture, spline, tab, stop, step, sealing surface, pivot point, axle, bearing surface, indicator to depict direction of fluid flow or magnetization, spring retaining collar, valve or valve actuator, or the magnet does not exhibit visible corrosion after 5 days immersion in 37° C. normal saline solution, or The magnet retains its full magnetic strength without exhibiting visible corrosion after 20 days immersion in 87° C. normal saline solution.

EXAMPLE 1

NdFeB ring magnets having a 32 Mega Gauss Oersteds $BH_{max}$ value and shaped like magnet 500 shown in FIG. 5 were coated with two 17 μm thick conformal coating layers of Parylene HT from Specialty Coating Systems, Inc. Prior to the application of the conformal coating layers, the magnets were gripped at different fixturing positions in order to ensure application of a continuous conformal coating layer. The thus-coated magnets were covered with polyethersulfone using a two-shot injection molding process to produce encapsulated, barrier-coated magnets like those shown in FIG. 6. The magnets were immersed for 28 days in 87° C. normal saline solution and then removed for evaluation. The magnets did not exhibit visible corrosion, and retained their full pre-immersion magnetic strength. Inductively-coupled plasma (ICP) mass spectrophotometric analysis of the saline solution found no detectable magnetic elements after such immersion compared to saline controls prepared without the immersed magnet.

COMPARISON EXAMPLE 1

NdFeB ring magnets like those used in Example 1 could be coated with a conformal coating made using Parylene C (—[$CH_2(C_6H_3Cl)CH_2$]$_n$—) from Specialty Coating Systems, Inc. Parylene C has a much lower melting point than that of polyethersulfone (viz., 290° C. for Parylene C and about 360° C. for polyethersulfone). Overmolding with polyethersulfone would be expected to destroy the conformal coating.

COMPARISON EXAMPLE 2

NdFeB ring magnets like those used in Example 1 could be coated with a conformal coating made using Parylene N (—[$CH_2(C_6H_4)CH_2$]$_n$—) from Specialty Coating Systems, Inc. Parylene N has a 420° C. melting point and thus might be overmolded with polyethersulfone. However, Parylene N also has less temperature resistance than Parylene HT (viz., a short term service temperature rating of 80° C. for Parylene N and 450° C. for Parylene HT, and a continuous service temperature rating of 60° C. for Parylene N and 350° C. for Parylene HT). Overmolding with polyethersulfone would require extra care in order not to compromise the conformal coating. Parylene N also has greater moisture vapor transmission than Parylene HT (viz., 0.59 g-mm/m²/day at 90% RH and 37° C. for Parylene N and 0.22 g-mm/m²/day at 100% RH and 37° C. for Parylene HT). A barrier made using Parylene N overmolded with polyethersulfone would be expected to provide less corrosion resistance than the barrier of Example 1.

COMPARISON EXAMPLE 3

NdFeB ring magnets like those used in Example 1 could be coated with a conformal coating made using Parylene D (—[$CH_2(C_6H_2Cl_2)CH_2$]$_n$—) from Specialty Coating Systems, Inc. Parylene D has a 380° C. melting point, which is slightly higher than that of polyethersulfone. Parylene D has less temperature resistance than Parylene HT (viz., Parylene D has a short term service temperature rating of 120° C. and a continuous service temperature rating of 100° C.). Overmolding with polyethersulfone would require extra care in order not to compromise the conformal coating.

EXAMPLE 2

The barrier-coated magnets described in Example 1 can be used as a magnetic rotor assembly to control the flow of CSF fluid in a shunt valve like that shown in the above-mentioned Bertrand et al. application. In an initial field trial, shunt valves containing the disclosed barrier-coated magnets and magnetic rotor assemblies were successfully surgically implanted in 13 human patients and confirmed to be operational. The rotor assemblies are expected to resist corrosion by bodily fluids, as well as unintended changes in rotor (viz., pressure) settings, demagnetization and re-magnetization when exposed to a 3 Tesla MRI field.

The complete disclosure of all cited patents, patent applications, technical bulletins and other publications are incorporated herein by reference as if individually incorporated.

Although specific and in some cases preferred embodiments have been illustrated and described, it will be appreciated by those of ordinary skill in the art that a variety of alternate or equivalent embodiments calculated to achieve the same purposes may be substituted for the specific embodiments shown and described above. This application is intended to cover any such adaptations or variations of the embodiments discussed herein. Therefore, it is manifestly intended that this invention be limited only by the claims and the equivalents thereof.

The invention claimed is:

1. A magnetic article comprising an NdFeB magnet having thereon a substantially continuous corrosion resistant barrier comprising a fluorinated parylene conformal coating covered with a polysulfone thermoplastic overlayer.

2. A magnetic article according to claim 1 wherein the magnet has a Maximum Energy Product $BH_{max}$ of at least 28 Mega Gauss Oersteds, an Intrinsic Coercive Force $H_{ci}$ of at least 10 kiloOersteads and a Curie Temperature $T_c$ of at least 300° C.

3. A magnetic article according to claim 1 wherein the magnet has a Maximum Energy Product $BH_{max}$ of at least 32 Mega Gauss Oersteds, an Intrinsic Coercive Force $_{ci}$ of at least 35 kiloOersteads and a Curie Temperature $T_c$ of at least 310 ° C.

4. A magnetic article according to claim 1 wherein the magnet comprises a bar, rod, ring, partial ring or plate.

5. A magnetic article according to claim 1 wherein the fluorinated parylene has fluoroaliphatic groups.

6. A magnetic article according to claim 1 wherein the conformal coating comprises poly(tetrafluoro-p-xylene).

7. A magnetic article according to claim 1 wherein the fluorinated parylene has fluoroaromatic groups.

8. A magnetic article according to claim 1 wherein the conformal coating comprises parylene VT-4.

9. A magnetic article according to claim 1 wherein the conformal coating has a thickness of 2 to 100 μm.

10. A magnetic article according to claim 1 wherein the overlayer comprises polyethersulfone.

11. A magnetic article according to claim 1 wherein the overlayer comprises sulfonated polyethersulfone or polyphenylsulfone.

12. A magnetic article according to claim 1 wherein the overlayer has an average thickness of 0.5 to 10 mm.

13. A magnetic article according to claim 1 wherein the overlayer has a variable thickness.

14. A magnetic article according to claim1 wherein the overlayer is an overmolding and is a layer made by injection molding.

15. A magnetic article according to claim 1 wherein the polysulfone melting point is less than the parylene melting point.

16. A magnetic article according to claim 1 wherein the conformal coating has a thickness less than 0.5 mm and the overlayer has an average thickness greater than 0.5mm.

17. A magnetic article according to claim 1 wherein the magnet or overlayer has a recess or protrusion.

18. A magnetic article according to claim 17 wherein the recess or protrusion comprises a groove, notch, detent, aperture, spline, tab, stop, step, sealing surface, pivot point, axle, hearing surface, indicator to depict direction of fluid flow or magnetization, spring retaining collar, valve or valve actuator.

19. A magnetic article according to claim 1 wherein the magnet does not exhibit visible corrosion after 5 days immersion in 37° C. normal saline solution.

20. A magnetic article according to claim 1 wherein the magnet retains its full magnetic strength without exhibiting visible corrosion after 20 days immersion in 87° C. normal saline solution.

21. A magnetic article comprising an NdFeB magnet having thereon a substantially continuous corrosion resistant barrier comprising a parylene conformal coating having a melting point of at least. about 430° C. and a moisture vapor transmission less than about 0.5 g-mm/m²/day at 90% RH and 37° C., the parylene conformal coating being covered with a polysulfone thermoplastic overlayer.

22. A magnetic article according to claim 21 wherein the conformal coating has a moisture vapor transmission less than about 0.4 g-mm/m²/day at 90% RH and 37° C.

23. A magnetic article according to claim 21 wherein the conformal coating has a moisture vapor transmission less than about 0.3 g-mm/m²/day at 90% RH and 37° C.

24. A method for making a coated magnetic article, which method comprises vapor depositing upon an NdFeB magnet a layer or layers of a poly(tetrafluoro-p-xylene) conformal coating, and applying molten polysulfone over the poly (tetrafluoro-p-xylene) conformal coating, to provide a substantially continuous corrosion resistant barrier over the magnet.

25. A method for making a coated magnetic article, which method comprises vapor depositing upon an NdFeB magnet a layer or layers of a parylene conformal coating having a melting point of at least about 430° C. and a moisture vapor transmission less than about 0.5 g-mm/m²/day at 90% RH and 37° C., and applying molten polysulfone over the parylene conformal coating, to provide a substantially continuous corrosion resistant barrier over the magnet.

26. An implantable medical device containing a coated magnetic article comprising an NdFeB magnet having thereon a substantially continuous corrosion resistant barrier comprising a poly(tetrafluoro-p-xylene) conformal coating covered with a polysulfbne thermoplastic overlayer.

27. An implantable medical device containing a coated magnetic article comprising an NdFeB magnet having thereon a substantially continuous corrosion resistant barrier comprising a paryiene conformal coating having a melting point of at least about 430° C. and a moisture vapor transmission less than about 0.5 g-mm/m²/day at 90% RH and 37° C., covered with a polysulfone thermoplastic overlayer.

* * * * *